(12) United States Patent
Maher et al.

(10) Patent No.: US 7,179,434 B1
(45) Date of Patent: *Feb. 20, 2007

(54) INTEGRATED APPARATUS FOR AROMATICS PRODUCTION

(75) Inventors: Gregory F. Maher, Aurora, IL (US); David A. Hamm, Hinsdale, IL (US)

(73) Assignee: UOP LLC, Des Plaines, IL (US)

( * ) Notice: Subject to any disclaimer, the term of this patent is extended or adjusted under 35 U.S.C. 154(b) by 191 days.

This patent is subject to a terminal disclaimer.

(21) Appl. No.: 10/936,086

(22) Filed: Sep. 8, 2004

(51) Int. Cl.
*B01J 8/00* (2006.01)
*C07C 5/22* (2006.01)

(52) U.S. Cl. ............... 422/236; 422/234; 585/470; 585/833

(58) Field of Classification Search ........... 585/470, 585/833; 422/236, 234
See application file for complete search history.

(56) References Cited

U.S. PATENT DOCUMENTS

| | | | |
|---|---|---|---|
| 3,996,305 A | 12/1976 | Berger | 260/672 T |
| 4,053,388 A | 10/1977 | Bailey | 208/89 |
| 4,241,036 A | 12/1980 | Flanigen et al. | 423/328 |
| 4,341,914 A | 7/1982 | Berger | 585/474 |
| 4,440,871 A | 4/1984 | Lok et al. | 502/214 |
| 4,537,754 A | 8/1985 | Casci et al. | 423/277 |
| 4,567,029 A | 1/1986 | Wilson et al. | 423/306 |
| 4,642,406 A | 2/1987 | Schmidt | 585/477 |
| 4,899,012 A | 2/1990 | Sachtler et al. | 585/482 |
| 5,296,208 A | 3/1994 | Lesch | 423/700 |
| 5,417,844 A | 5/1995 | Boitiaux et al. | 208/143 |
| 5,658,453 A | 8/1997 | Russ et al. | 208/62 |
| 5,665,223 A | 9/1997 | Bogdan | 208/138 |
| 5,723,710 A | 3/1998 | Gajda et al. | 585/467 |
| 5,763,720 A | 6/1998 | Buchanan et al. | 585/475 |
| 5,847,256 A | 12/1998 | Ichioka et al. | 585/470 |

*Primary Examiner*—Thuan Dinh Dang
(74) *Attorney, Agent, or Firm*—John G. Tolomei; James C. Paschall; Maryann Maas

(57) ABSTRACT

Enabling a transalkylation process to handle both $C_{10}$ alkylaromatics and unextracted toluene permits the following improvements to be realized. No longer extracting toluene allows a reformate-splitter column to be eliminated. The extraction unit can be moved to the overhead of a benzene column that is also closely integrated with the transalkylation unit. No longer requiring a rigorous split between $C_9$ and $C_{10}$ alkylaromatics allows a heavy aromatics column to be eliminated. Such an enabled transalkylation process requires stabilization of a transalkylation catalyst through the introduction of a metal function. These improvements result in an aromatics complex apparatus with savings on inside battery limits curve costs and an improvement on the return on investment in such a complex.

16 Claims, 2 Drawing Sheets

US 7,179,434 B1

INTEGRATED APPARATUS FOR AROMATICS PRODUCTION

FIELD OF THE INVENTION

This invention relates to an aromatics complex flow scheme, which is a combination of apparatus zones using process units that can be used to convert naphtha into basic petrochemical intermediates of benzene, toluene, and xylene. Based on a metal catalyzed transalkylation process that handles unextracted toluene and heavier aromatics and an olefin saturation process, the improved flow scheme removes items of equipment and processing steps, such as a reformate splitter column and a heavy aromatics column, resulting in significant economic benefits when producing xylene isomers.

BACKGROUND OF THE INVENTION

Most new aromatics complexes are designed to maximize the yield of benzene and para-xylene. Benzene is a versatile petrochemical building block used in many different products based on its derivation including ethylbenzene, cumene, and cyclohexane. Para-xylene is also an important building block, which is used almost exclusively for the production of polyester fibers, resins, and films formed via terephthalic acid or dimethyl terephthalate intermediates. Accordingly, an aromatics complex may be configured in many different ways depending on the desired products, available feedstocks, and investment capital available. A wide range of options permits flexibility in varying the product slate balance of benzene and para-xylene to meet downstream processing requirements.

A prior art aromatics complex flow scheme has been disclosed by Meyers in the HANDBOOK OF PETROLEUM REFINING PROCESSES, 2d. Edition in 1997 by McGraw-Hill.

U.S. Pat. No. 3,996,305 to Berger discloses a fractionation scheme primarily directed to transalkylation of toluene and $C_9$ alkylaromatics in order to produce benzene and xylene. The transalkylation process is also combined with an aromatics extraction process. The fractionation scheme includes a single column with two streams entering and with three streams exiting the column for integrated economic benefits.

U.S. Pat. No. 4,053,388 to Bailey discloses a process for preparing aromatics from naphtha that achieves an increased yield by integrating a catalytic reforming unit with a thermal hydrocracking unit. The aromatics are recovered in a complex flow scheme using extractive distillation, transalkylation, para-xylene separation, and xylene isomerization processes. A rerun column for heavy aromatics is also disclosed.

U.S. Pat. No. 4,341,914 to Berger discloses a transalkylation process with recycle of $C_{10}$ alkylaromatics in order to increase yield of xylenes from the process. The transalkylation process is also preferably integrated with a para-xylene separation zone and a xylene isomerization zone operated as a continuous loop receiving mixed xylenes from the transalkylation zone feedstock and effluent fractionation zones.

U.S. Pat. No. 4,642,406 to Schmidt discloses a high severity process for xylene production that employs a transalkylation zone that simultaneously performs as an isomerization zone over a nonmetal catalyst. High quality benzene is produced along with a mixture of xylenes, which allows para-xylene to be separated by absorptive separation from the mixture with the isomer-depleted stream being passed back to the transalkylation zone.

U.S. Pat. No. 5,417,844 to Boitiaux et al. discloses a process for the selective dehydrogenation of olefins in steam cracking petrol in the presence of a nickel catalyst and is characterized in that prior to the use of the catalyst, a sulfur-containing organic compound is incorporated into the catalyst outside of the reactor prior to use.

U.S. Pat. No. 5,658,453 to Russ et al. discloses an integrated reforming and olefin saturation process. The olefin saturation reaction uses a mixed vapor phase with addition of hydrogen gas to a reformate liquid in contact with a refractory inorganic oxide containing preferably a platinum-group metal and optionally a metal modifier.

U.S. Pat. No. 5,763,720 to Buchanan et al. discloses a transalkylation process for producing benzene and xylenes by contacting a $C_9^+$ alkylaromatics with benzene and/or toluene over a catalyst comprising a zeolite such as ZSM-12 and a hydrogenation noble metal such as platinum. Sulfur or steam is used to treat the catalyst.

U.S. Pat. No. 5,847,256 to Ichioka et al. discloses a process for producing xylene from a feedstock containing $C_9$ alkylaromatics with the aid of a catalyst with a zeolite that is preferably mordenite and with a metal that is preferably rhenium.

SUMMARY OF THE INVENTION

An aromatics complex flow scheme with an enabled transalkylation process requires stabilization of a transalkylation catalyst through the introduction of a metal function. Enabling a transalkylation process to handle both $C_{10}$ alkylaromatics and unextracted toluene permits the following flow scheme improvements to be realized. By using toluene without first passing it to an extraction unit, the flow scheme omits a reformate-splitter column. The concomitantly smaller capacity extraction unit is moved to the overhead of a benzene column. By only extracting benzene, simple extractive distillation is used, since a more expensive combined liquid-liquid extraction method is only required for heavier contaminants. By using both $C_9$ and $C_{10}$ alkylaromatics in an enabled transalkylation unit, the flow scheme further omits a heavy aromatics column.

Another embodiment of the present invention comprises an apparatus that is based on the process steps, which efficiently converts naphtha into para-xylene. A transalkylation column may be used to eliminate the separate benzene column. A xylene column may be used with a side-cut or side-draw conduit instead of a separate heavy aromatics column.

Additional objects, embodiments and details of this invention can be obtained from the following detailed description of the invention.

DETAILED DESCRIPTION OF THE INVENTION

Figure 1:
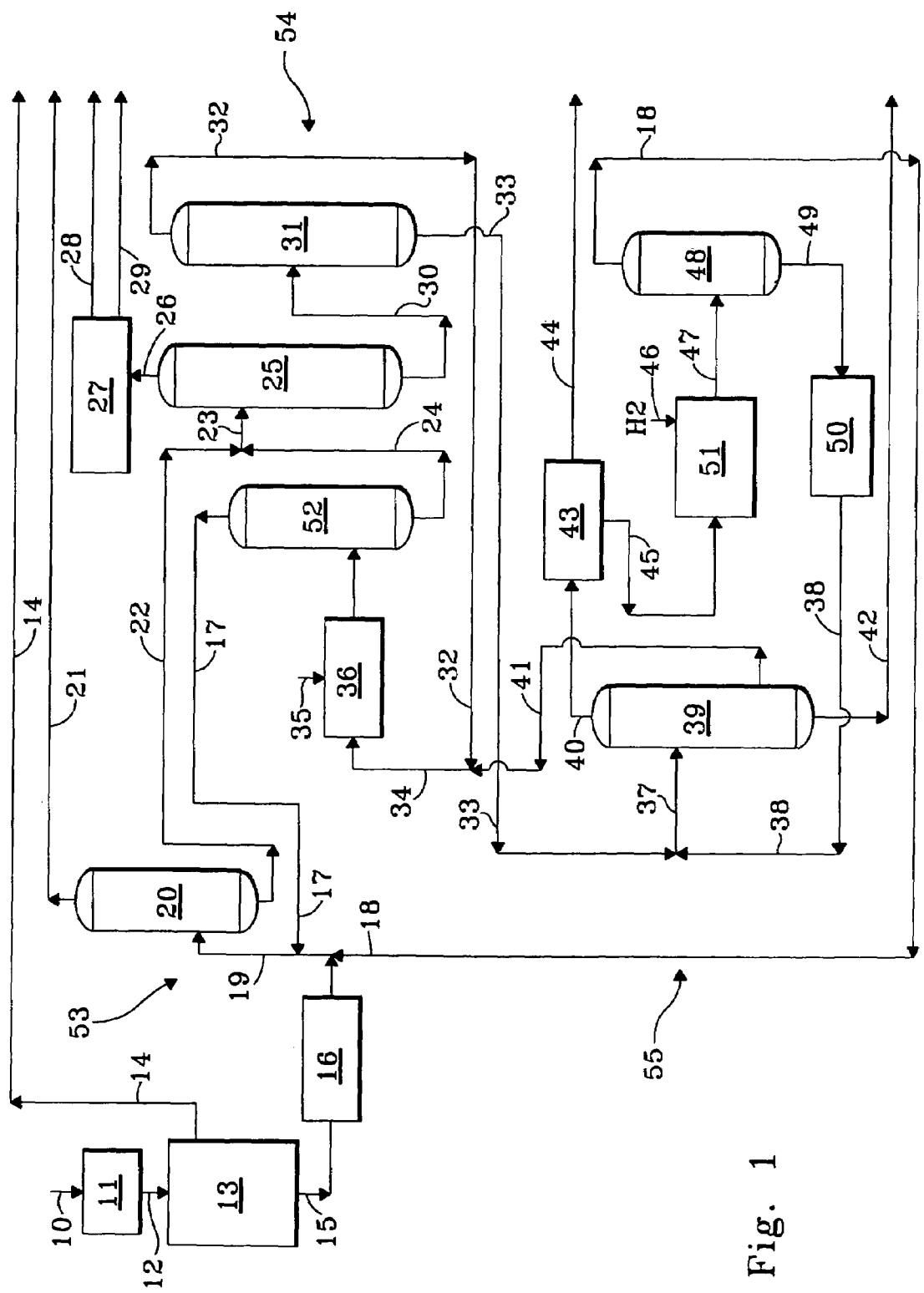
FIG. 1 shows an aromatics complex flow scheme of the present invention, which includes olefin saturation and a metal stabilized transalkylation catalyst.

Feed to the complex may be naphtha, but can also be pygas, imported mixed xylene, or imported toluene. Naphtha fed to an aromatics complex is first hydrotreated to remove sulfur and nitrogen compounds to less than about 0.5 wt-ppm before passing the treated naphtha on to a reforming unit 13. Naphtha hydrotreating occurs by contacting naphtha in a line 10 with a naphtha hydrotreating catalyst under naphtha hydrotreating conditions in a unit 11. Note that the term "unit" will be used throughout the description herein to refer to various process zones and such a "zone" may be understood as including process equipment and apparatus pieces such as reactor vessels, heaters, separators, exchangers, piping, pumps, compressors, controllers and any and all other equipment and machinery necessary to perform each process without limitation and so understood to be part of such units or zones by one of ordinary skill in the art of each process.

The naphtha hydrotreating catalyst is typically composed of a first component of cobalt oxide or nickel oxide, along with a second component of molybdenum oxide or tungsten oxide, and a third component inorganic oxide support, which is typically a high purity alumina. Generally good results are achieved when the cobalt oxide or nickel oxide component is in the range of about 1 to about 5 wt-% and the molybdenum oxide component is in the range of about 6 to about 25 wt-%. The alumina (or aluminum oxide) is set to balance the composition of the naphtha hydrotreating catalyst to sum all components up to 100 wt-%. One hydrotreating catalyst for use in the present invention is disclosed in U.S. Pat. No. 5,723,710, the teachings of which are incorporated herein by reference. Typical hydrotreating conditions include a liquid hourly space velocity (LHSV) from about 1.0 to about 5.0 $hr^{-1}$, a ratio of hydrogen to hydrocarbon (or naphtha feedstock) from about 50 to about 135 $Nm^3/m^3$, and a pressure from about 10 to about 35 $kg/cm^2$.

In the reforming unit 13, paraffins and naphthenes are converted to aromatics. This is the only unit in the complex that actually creates aromatic rings. The other units in the complex separate the various aromatic components into individual products and convert various aromatic species into higher-value products. The reforming unit 13 is usually designed to run at very high severity, equivalent to producing about 100 to about 106 Research Octane Number (RON) gasoline reformate, in order to maximize the production of aromatics. This high severity operation also extinguishes virtually all non-aromatic impurities in the $C_8^+$ fraction of reformate, and eliminates the need for extraction of the $C_8$ and $C_9$ aromatics.

In the reforming unit 13, hydrotreated naphtha from a line 12 is contacted with a reforming catalyst under reforming conditions. The reforming catalyst is typically composed of a first component platinum-group metal, a second component modifier metal, and a third component inorganic-oxide support, which is typically high purity alumina. Generally good results are achieved when the platinum-group metal is in the range of about 0.01 to about 2.0 wt-% and the modifier metal component is in the range of about 0.01 to about 5 wt-%. The alumina is set to balance the composition of the naphtha hydrotreating catalyst to sum all components up to 100 wt-%. The platinum-group metal is selected from platinum, palladium, rhodium, ruthenium, osmium, and iridium. The preferred platinum-group metal component is platinum. The metal modifiers may include rhenium, tin, germanium, lead, cobalt, nickel, indium, gallium, zinc, uranium, dysprosium, thallium, and mixtures thereof. One reforming catalyst for use in the present invention is disclosed in U.S. Pat. No. 5,665,223, the teachings of which are incorporated herein by reference. Typical reforming conditions include a liquid hourly space velocity from about 1.0 to about 5.0 $hr^{-1}$, a ratio of hydrogen to hydrocarbon from about 1 to about 10 moles of hydrogen per mole of hydrocarbon feed entering the reforming zone, and a pressure from about 2.5 to about 35 $kg/cm^2$. Hydrogen produced in the reforming unit 13 exits in a line 14.

Figure 2:
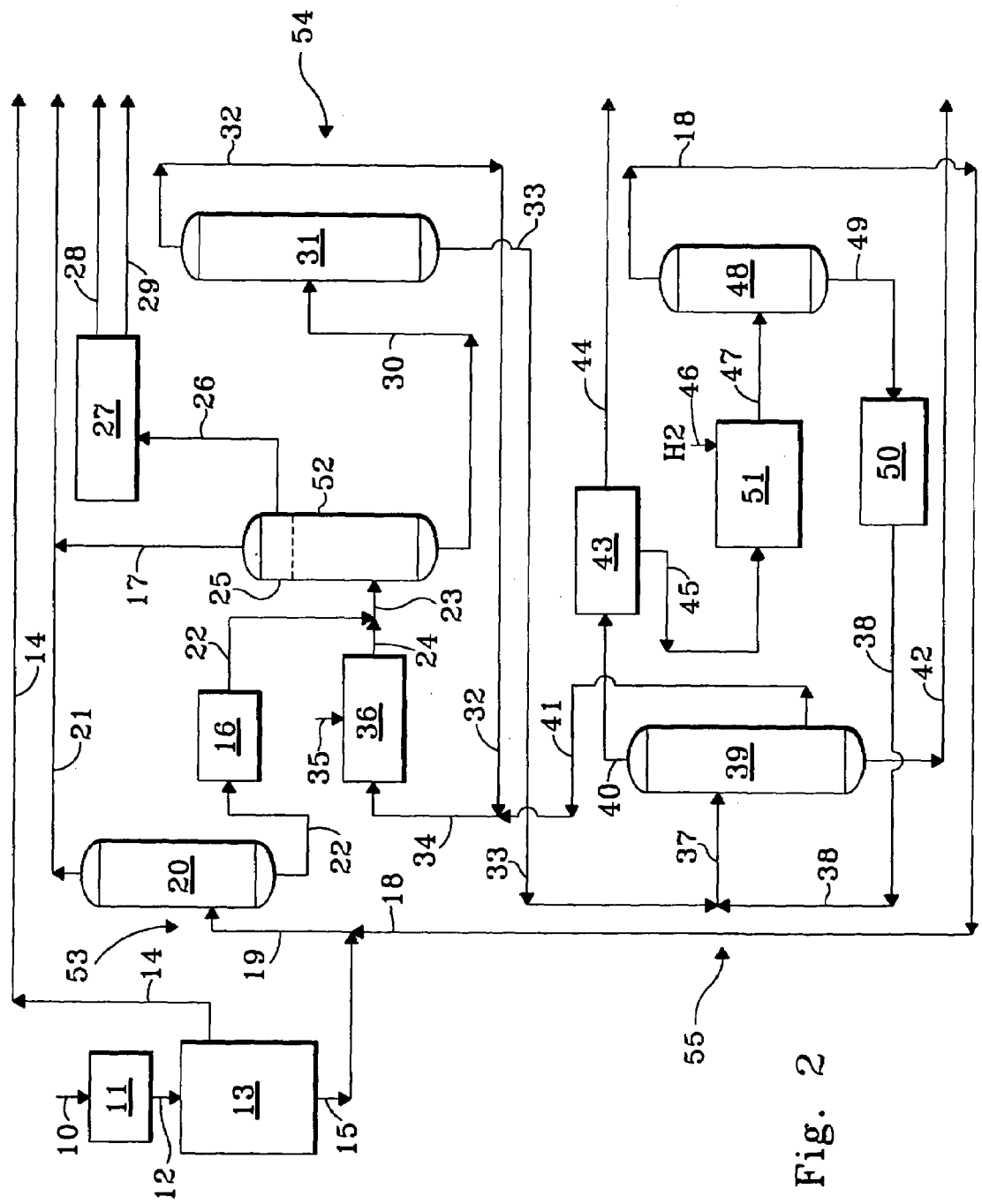
FIG. 2 shows an alternate embodiment of the present invention, which includes a flow scheme based around a transalkylation stripper column with a stabilizer section that replaces a benzene column.

The reformate product from the reforming unit 13 in a line 15 is sent to a debutanizer zone 53, which typically comprises a debutanizer column 20 that strips off the light end hydrocarbons (butanes and lighter) in a line 21. The debutanizer zone 53 may also comprise at least one olefin saturation zone 16, which may be placed upstream or downstream from the debutanizer column 20. FIG. 1 illustrates an upstream option while FIG. 2 illustrates a downstream option. Moreover, streams from other units in the aromatics complex may also be sent via a line 19 to the debutanizer column 20 for stripping. These other units include the transalkylation zone, which sends a transalkylation stripper-overhead stream in a line 17, and the isomerization zone, which sends a deheptanizer overhead stream in a line 18. Both of these units are described in greater detail below.

The olefin saturation zone 16 may consist of the well-known clay treating means or other means to treat residual olefin contaminants. Clay treating means includes the optional use of hydrogen as an olefin saturation catalyst means. Accordingly, the olefin saturation zone 16 comprises an olefin saturation catalyst operating under olefin saturation conditions.

Suitable olefin saturation catalysts in the present invention contain elemental nickel or a platinum-group component preferably supported on an inorganic oxide support, which is typically alumina. In the case where the elemental nickel is present on a support, the nickel is preferably present in an amount from about 2 to about 40 wt-% of the total catalyst weight. One catalyst for use in the present invention is disclosed in U.S. Pat. No. 5,658,453, the teachings of which are incorporated herein by reference. Alternatively, clay itself is a preferred olefin saturation catalyst, optionally used with hydrogen, and such clay may be defined as a common earth of various colors, compact and brittle when dry, but plastic and tenacious when wet. Clay is a hydrous aluminum silicate generally mixed with powdered feldspar, quartz, sand, iron oxide and various other minerals and is formed from the decomposition of aluminous rocks such as feldspar in granite. Any suitable clay which demonstrates the ability to selectively saturate olefins may be utilized in the present invention. Highly preferred clays include attapulgus clay and Montmorillonite clay. It is believed that the natural iron content of many types of clay contributes to the ability of clay to selectively saturate the olefin compounds in an aromatic feedstock while preserving the aromatic compounds. Typical olefin saturation conditions include a temperature from about 20° to about 200° C., a pressure from about 5 to about 70 $kg/cm^2$ and a stoichiometric ratio of hydrogen, if present, to olefins from about 0.1:1 to about 15:1.

The debutanized reformate comprising aromatics in a line 22 is combined with a transalkylation stripper-bottoms stream in a line 24 and sent to a benzene-toluene (BT) fractionation zone 54 via a line 23. The BT fractionation zone 54 generally comprises at least one column, and usually comprises a benzene column 25 and a toluene column 31. However, the benzene column 25 may be eliminated in favor of a transalkylation stripper column 52, with a stabilizer section sufficient to produce a suitable benzene stream as shown in FIG. 2. The BT fractionation zone 54 produces a benzene-enriched stream in a line 26, a toluene-enriched stream in a line 32, and a xylene-plus-enriched stream in a line 33. Typically, the benzene-enriched stream in the line 26 is produced from the overhead of the benzene column 25, with the bottom of the benzene column 25 being sent via a line 30 to feed the toluene column 31. The toluene-enriched stream in the line 32 is produced from the overhead of the toluene column 31 and sent to a transalkylation unit 36, with the bottom of the toluene column 31 producing the xylene-plus-enriched stream in the line 33. The xylene-plus-enriched stream in the line 33 from the bottom of the toluene column 31 is sent to a xylene recovery section 55 of the aromatics complex described below.

The benzene-enriched stream in the line 26 is sent to an extractive distillation zone 27 which produces a high purity benzene product stream in a line 29 and rejects a by-product raffinate stream in a line 28. The raffinate stream may be blended into gasoline, used as feedstock for an ethylene plant, or converted into additional benzene by recycling to the reforming unit 13. The use of extractive distillation instead of liquid-liquid extraction or combined liquid-liquid extraction/extractive distillation processes results in an economic improvement.

Extractive distillation is a technique for separating mixtures of components having nearly equal volatility and having nearly the same boiling point. It is difficult to separate the components of such mixtures by conventional fractional distillation. In extractive distillation, a solvent is introduced into a main extractive-distillation column above the entry point of the hydrocarbon-containing fluid mixture that is to be separated. The solvent affects the volatility of the hydrocarbon-containing fluid component boiling at a higher temperature differently than the hydrocarbon-containing fluid component boiling at a lower temperature sufficiently to facilitate the separation of the various hydrocarbon-containing fluid components by distillation and such solvent exits with the bottoms fraction. Suitable solvents include tetrahydrothiophene 1,1-dioxide (or sulfolane), diethylene glycol, triethylene glycol, or tetraethylene glycol. The raffinate stream in the line 28 comprising nonaromatic compounds exits the extractive distillation zone 27 overhead of the main extractive-distillation column, while the bottoms fraction containing solvent and benzene exits below the main extractive-distillation column. The bottoms stream from the main extractive-distillation column is sent to a solvent-recovery column, where benzene is recovered overhead in the line 29 and the solvent is recovered from the bottom and passed back to the main extractive-distillation column. The recovery of high purity benzene in the line 29 from the extractive distillation zone 27 typically exceeds 99 wt-%.

The toluene-enriched stream in the line 32 is usually blended with a stream in a line 41 rich in $C_9$ and $C_{10}$ alkylaromatics produced by a xylene column 39 and charged via a line 34 to the transalkylation unit 36 for production of additional xylenes and benzene. In the transalkylation unit 36, the feed is contacted with a transalkylation catalyst under transalkylation conditions. The preferred catalyst is a metal stabilized transalkylation catalyst. Such catalyst comprises a solid-acid component, a metal component, and an inorganic oxide component. The solid-acid component typically is either a pentasil zeolite, which include the structures of MFI, MEL, MTW, MTT and FER (IUPAC Commission on Zeolite Nomenclature), a beta zeolite, or a mordenite. Preferably it is mordenite zeolite. Other suitable solid-acid components include mazzite, NES type zeolite, EU-1, MAPO-36, MAPSO-31, SAPO-5, SAPO-11, SAPO-41. Preferred mazzite zeolites include Zeolite Omega. The synthesis of the Zeolite Omega is described in U.S. Pat. No. 4,241,036. European Patent Application EP 0 378 916 A1 describes NES type zeolite and a method for preparing NU-87. The EUO structural-type EU-1 zeolite is described in U.S. Pat. No. 4,537,754. MAPO-36 is described in U.S. Pat. No. 4,567,029. MAPSO-31 is described in U.S. Pat. No. 5,296,208 and typical SAPO compositions are described in U.S. Pat. No. 4,440,871 including SAPO-5, SAPO-11, SAPO-41

The metal component typically is a noble metal or base metal. The noble metal is a platinum-group metal is selected from platinum, palladium, rhodium, ruthenium, osmium, and iridium. The base metal is selected from the group consisting of rhenium, tin, germanium, lead, cobalt, nickel, indium, gallium, zinc, uranium, dysprosium, thallium, and mixtures thereof. The base metal may be combined with another base metal, or with a noble metal. Preferably the metal component comprises rhenium. Suitable metal amounts in the transalkylation catalyst range from about 0.01 to about 10 wt-%, with the range from about 0.1 to about 3 wt-% being preferred, and the range from about 0.1 to about 1 wt-% being highly preferred. Suitable zeolite amounts in the catalyst range from about 1 to about 99 wt-%, preferably between about 10 to about 90 wt-%, and more preferably between about 25 to about 75 wt-%. The balance of the catalyst is composed of a refractory binder or matrix that is optionally utilized to facilitate fabrication of the catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, phosphate, zinc oxide and silica. Alumina is a preferred binder. One transalkylation catalyst for use in the present invention is disclosed in U.S. Pat. No. 5,847,256, the teachings of which are incorporated herein by reference Conditions employed in the transalkylation zone normally include a temperature of from about 200° to about 540° C. The transalkylation zone is operated at moderately elevated pressures broadly ranging from about 1 to about 60 kg/cm². The transalkylation reaction can be effected over a wide range of space velocities, with higher space velocities effecting a higher ratio of para-xylene at the expense of conversion. Liquid hourly space velocity generally is in the range of from about 0.1 to about 20 hr$^{-1}$. The feedstock is preferably transalkylated in the vapor phase and in the presence of hydrogen supplied via a line 35. If transalkylated in the liquid phase, then the presence of hydrogen is optional. If present, free hydrogen is associated with the feedstock and recycled hydrocarbons in an amount of about 0.1 moles per mole of alkylaromatics up to about 10 moles per mole of alkylaromatic. This ratio of hydrogen to alkylaromatic is also referred to as hydrogen to hydrocarbon ratio.

The effluent from the transalkylation unit 36 is sent to the transalkylation stripper column 52 to remove light ends, then sent to the BT fractionation zone 54 through the lines 24 and 23. There the benzene product is recovered, and the xylenes are fractionated out and sent to the xylene recovery section 55 via the xylene plus enriched stream in the line 33. The overhead material from the transalkylation stripper column 52 is normally recycled back via the line 17 to the reforming unit debutanizer for recovery of residual benzene. Alternatively, a stabilizer section or column is placed on or after the transalkylation stripper column 52. This transalkylation stabilizer section can produce a benzene-enriched stream suitable for extractive distillation, and eliminate the need for a separate benzene column in the BT fractionation section as shown in FIG. 2, which shows section 25 on top of column 52. Such a stabilizer or stripper column from the transalkylation zone is thus alternatively encompassed in the definition of the BT fractionation zone 54 when the separate benzene column 25 is eliminated. The transalkylation stripper column 52 can also accept treated product from the olefin saturation zone or overhead from the alkylaromatic isomerization deheptanizer column that would normally be recycled back to the reforming unit debutanizer column 20.

As noted above, the xylene-plus-enriched stream in the line 33 from the bottom of the toluene column 31 is sent to the xylene recovery section 55 of the aromatics complex. This section of the aromatics complex comprises at least one xylene column 39, and generally will further include a process unit for separation of at least one xylene isomer, which is typically the para-xylene product from the aromatics complex but may instead be a meta-xylene isomer. Hereinafter the xylene-isomer separation zone will be described in terms of a para-xylene isomer. Preferably such a para-xylene separation zone 43 is operated in conjunction with an isomerization unit 51 for isomerization of the remaining alkylaromatic compounds back to an equilibrium or near equilibrium mixture containing para-xylene, which can be recycled around again for further recovery in a loop-wise fashion. Accordingly, the xylene-plus-enriched stream in the line 33, which may be blended with a recycle stream in a line 38 to form a stream in a line 37, is charged to the xylene column 39. The xylene column 39 is designed to rerun a feed stream in a line 40 to the para-xylene separation zone 43 down to very low levels of $C_9$ alkylaromatics ($A_9$) concentration. $A_9$ compounds may build up in a desorbent circulation loop within the para-xylene separation zone 43, so it is more efficient to remove this material upstream in the xylene column 39. The overhead feed stream in the line 40 from the xylene column 39 is charged directly to the para-xylene separation zone 43.

Material from the lower part of the xylene column 39 is withdrawn as a stream rich in $C_9$ and $C_{10}$ alkylaromatics via the line 41, which is then sent to the transalkylation unit 36 for production of additional xylenes and benzene. The stream in the line 41 taken as a sidecut stream on the xylene column (which eliminates a heavy aromatics column) is really enabled by the metal stabilized transalkylation catalyst. A separate column doing a rigorous split to keep coke precursors such as methyl indan or naphthalene out of the stream is no longer needed because the metal stabilized transalkylation catalyst can handle them without significant deactivation due to coking. Any remaining $C_{11}^+$ material is rejected from the bottom of the xylene column 39 via a line 42. Another embodiment is to just send the whole xylene column bottoms stream to the transalkylation unit instead of the sidecut stream.

Alternatively, if ortho-xylene is to be produced in the complex, the xylene column is designed to make a split between meta and ortho-xylene and drop a targeted amount of orthoxylene to the bottoms. The xylene column bottoms is then sent to an ortho-xylene column (not shown) where high purity ortho-xylene product is recovered overhead. Material from the lower part of the ortho-xylene column is withdrawn as a stream rich in $C_9$ and $C_{10}$ alkylaromatics then sent to the transalkylation unit. Any remaining $C_{11}^+$ material is rejected from the bottom of the ortho-xylene column.

The para-xylene separation zone 43 may be based on a fractional crystallization process or an adsorptive separation process, both of which are well known in the art, and preferably is based on the adsorptive separation process. Such adsorptive separation can recover over 99 wt-% pure para-xylene in a line 44 at high recovery per pass. Any residual toluene in the feed to the separation unit is extracted along with the para-xylene, fractionated out in a finishing column within the unit, and then optionally recycled to the transalkylation stripper column 52. Thus, the raffinate from the para-xylene separation zone 43 is almost entirely depleted of para-xylene, to a level usually of less than 1 wt-%. The raffinate is sent via a line 45 to the alkylaromatics isomerization unit 51, where additional para-xylene is produced by reestablishing an equilibrium or near-equilibrium distribution of xylene isomers. Any ethylbenzene in the para-xylene separation unit raffinate is either converted to additional xylenes or converted to benzene by dealkylation, depending upon the type of isomerization catalyst used.

In the alkylaromatic isomerization unit 51, the raffinate stream in the line 45 is contacted with an isomerization catalyst under isomerization conditions. The isomerization catalyst is typically composed of a molecular sieve component, a metal component, and an inorganic oxide component. Selection of the molecular sieve component allows control over the catalyst performance between ethylbenzene isomerization and ethylbenzene dealkylation depending on overall demand for benzene. Consequently, the molecular sieve may be either a zeolitic aluminosilicate or a non-zeolitic molecular sieve. The zeolitic aluminosilicate (or zeolite) component typically is either a pentasil zeolite, which include the structures of MFI, MEL, MTW, MTT and FER (IUPAC Commission on Zeolite Nomenclature), a beta zeolite, or a mordenite. The non-zeolitic molecular sieve is typically one or more of the AEL framework types, especially SAPO-11, or one or more of the ATO framework types, especially MAPSO-31, according to the "Atlas of Zeolite Structure Types" (Butterworth-Heineman, Boston, Mass., 3rd ed. 1992). The metal component typically is a noble metal component, and may include an optional base metal modifier component in addition to the noble metal or in place of the noble metal. The noble metal is a platinum-group metal is selected from platinum, palladium, rhodium, ruthenium, osmium, and iridium. The base metal is selected from the group consisting of rhenium, tin, germanium, lead, cobalt, nickel, indium, gallium, zinc, uranium, dysprosium, thallium, and mixtures thereof. The base metal may be combined with another base metal, or with a noble metal. Suitable total metal amounts in the isomerization catalyst range from about 0.01 to about 10 wt-%, with the range from about 0.1 to about 3 wt-% preferred. Suitable zeolite amounts in the catalyst range from about 1 to about 99 wt-%, preferably between about 10 to about 90 wt-%, and more preferably between about 25 to about 75 wt-%. The balance of the catalyst is composed of inorganic oxide binder, typically alumina. One isomerization catalyst for use in the present invention is disclosed in U.S. Pat. No. 4,899,012, the teachings of which are incorporated herein by reference.

Typical isomerization conditions include a temperature in the range from about 0° to about 600° C. and a pressure from atmospheric to about 50 kg/cm$^3$. The liquid hourly hydrocarbon space velocity of the feedstock relative to the volume of catalyst is from about 0.1 to about 30 hr$^{-1}$. The hydrocarbon contacts the catalyst in admixture with a gaseous hydrogen-containing stream in a line 46 at a hydrogen-to-hydrocarbon mole ratio of from about 0.5:1 to 15:1 or more, and preferably a ratio of from about 0.5 to 10. If liquid phase conditions are used for isomerization, then no hydrogen is added to the unit.

The effluent from the isomerization unit 51 is sent via a line 47 to a deheptanizer column 48. A bottoms stream in a line 49 from the deheptanizer column 48 is treated to remove olefins, if necessary, in an olefin saturation unit 50 with the olefin saturation methods described above. An alternative is to put the olefin saturation unit 50 after the isomerization unit 51 and use the deheptanizer column 48 to remove residual hydrogen. If the catalyst used in the isomerization unit 51 is the ethylbenzene dealkylation type, then olefin saturation may not be required at all.

The deheptanizer bottoms stream in the line 49, after olefin treatment, is then recycled back to the xylene column 39 via the line 38. In this way, all the $C_8$ aromatics are continually recycled within the xylenes recovery section of the complex until they exit the aromatics complex as para-xylene, benzene, or optionally ortho-xylene. The overhead from the deheptanizer column 48 is normally recycled back via the line 18 to the reforming unit debutanizer column 20 for recovery of residual benzene. Alternatively, the overhead liquid is recycled back to the transalkylation stripper column 52.

Accordingly, the aromatics complex of the present invention displays excellent economic benefits. These improvements result in an aromatics complex with savings on inside battery limits curve costs and an improvement on the return on investment in such a complex.

What is claimed is:

1. An integrated apparatus for producing xylene isomers from a catalytic reformate stream comprising:
    (a) a fractionation zone comprising a debutanizer column wherein the reformate stream is split into a light stream comprising butanes and lighter components and a debutanized reformate stream;
    (b) a second fractionation zone comprising a toluene column, wherein the debutanized reformate stream and at least a portion of a transalkylation product stream are separated to produce a toluene-enriched stream, and a xylene-plus-enriched stream;
    (c) a transalkylation zone comprising a reactor wherein the toluene-enriched stream and a xylene-column stream rich in $C_9$ and $C_{10}$ alkylaromatics are contacted with a metal-stabilized transalkylation catalyst under transalkylation conditions to produce the transalkylation product stream of step (b); and
    (d) a xylene recovery section comprising a xylene fractionation column and a xylene-isomer separation zone, wherein the xylene fractionation column separates the xylene-plus-enriched stream of step (b) to provide the xylene-column stream rich in $C_9$ and $C_{10}$ alkylaromatics of step (c) and an overhead xylene stream, and wherein the xylene-isomer separation zone concentrates the overhead xylene stream into a xylene isomer enriched product stream which is recovered as a product stream of said apparatus.

2. The apparatus of claim 1 wherein the debutanizer fractionation zone further comprises an olefin saturation zone.

3. The apparatus of claim 1 wherein the xylene recovery section further comprises an alkylaromatics isomerization zone.

4. The apparatus of claim 3 wherein alkylaromatics isomerization zone further comprises a deheptanizer fractionation zone having at least one deheptanizer column and optionally at least one olefin saturation zone.

5. The apparatus of claim 1 wherein the xylene column is further characterized by having a means for withdrawing as a sidecut the stream rich in $C_9$ and $C_{10}$ alkylaromatics.

6. The apparatus of claim 1 wherein the xylene recovery section further comprises an ortho-xylene column.

7. The apparatus of claim 1 wherein the transalkylation zone further comprises a transalkylation stripper column.

8. The apparatus of claim 7 wherein the transalkylation stripper column further comprises a stabilizer section.

9. The apparatus of claim 7 wherein the transalkylation stripper column produces a benzene-enriched stream.

10. The apparatus of claim 9 further comprising an extractive-distillation zone having a main distillation column, wherein the benzene-enriched stream produces a raffinate stream and a benzene product.

11. The apparatus of claim 1 wherein the xylene-isomer separation zone is an adsorptive separation process comprising a finishing column.

12. An integrated apparatus for producing benzene and xylene isomers from a catalytic reformate stream comprising:
    (a) a debutanizer fractionation zone comprising a debutanizer column and an olefin saturation zone, wherein the reformate stream is separated into a light stream and a debutanized aromatics stream;
    (b) a second fractionation zone comprising a transalkylation stripper column and a toluene column, wherein the debutanized aromatics stream along with at least a portion of a transalkylation product stream is introduced to the transalkylation stripper column to produce a benzene-enriched stream and the remainder is introduced to the toluene column to produce a toluene-enriched stream, and a xylene-plus-enriched stream;
    (c) an extractive-distillation zone comprising a main distillation column, wherein the benzene-enriched stream produces a raffinate stream and a benzene product which is recovered as a product stream from said apparatus;
    (d) a xylene column, wherein a xylene-column stream rich in $C_9$ and $C_{10}$ alkylaromatics is produced as a sidecut from the xylene column;
    (e) a transalkylation zone comprising a reactor, wherein the toluene-enriched stream is provided with the xylene-column stream rich in $C_9$ and $C_{10}$ alkylaromatics and contacted with a metal-stabilized transalkylation catalyst under transalkylation conditions to produce the transalkylation product stream of step (b); and
    (f) a xylene recovery section comprising a xylene fractionation zone and a xylene-isomer separation zone, wherein the xylene fractionation zone comprises the xylene column of step (d) that separates the xylene-plus-enriched stream of step (b) into the xylene-column stream rich in $C_9$ and $C_{10}$ alkylaromatics and an overhead xylene stream, and wherein the xylene-isomer separation zone concentrates the overhead xylene stream into a xylene isomer enriched product stream which is recovered as a product stream of said apparatus.

13. The apparatus of claim 12 wherein the xylene recovery section further comprises an alkylaromatics isomerization zone.

14. The apparatus of claim 13 wherein alkylaromatics isomerization zone further comprises a deheptanizer fractionation zone having at least one deheptanizer column and optionally at least one olefin saturation zone.

15. The apparatus of claim 12 wherein the xylene recovery section further comprises an ortho-xylene column.

16. The apparatus of claim 12 wherein the xylene-isomer separation zone is an adsorptive separation process or a fractional crystallization process.

* * * * *